United States Patent
Borrel

(10) Patent No.: US 11,262,339 B2
(45) Date of Patent: Mar. 1, 2022

(54) REMOTE SENSOR CALIBRATION SYSTEM

(71) Applicant: Airlib Inc., Scottsdale, AZ (US)

(72) Inventor: Herve Patrick Borrel, Scottsdale, AZ (US)

(*) Notice: Subject to any disclaimer, the term of this patent is extended or adjusted under 35 U.S.C. 154(b) by 208 days.

(21) Appl. No.: 16/586,937

(22) Filed: Sep. 28, 2019

(65) Prior Publication Data
US 2020/0110065 A1 Apr. 9, 2020

Related U.S. Application Data

(60) Provisional application No. 62/743,459, filed on Oct. 9, 2018.

(51) Int. Cl.
*G01N 33/00* (2006.01)
*B60H 1/00* (2006.01)
*G01D 18/00* (2006.01)

(52) U.S. Cl.
CPC ......... *G01N 33/0006* (2013.01); *B60H 1/008* (2013.01); *G01D 18/008* (2013.01)

(58) Field of Classification Search
CPC ... G01N 33/0006; B60H 1/008; G01D 18/008
See application file for complete search history.

(56) References Cited

U.S. PATENT DOCUMENTS

| | | | |
|---|---|---|---|
| 4,155,038 A | 5/1979 | Merklinger | |
| 8,296,225 B2 | 10/2012 | Maddipati | |
| 9,332,322 B2 | 5/2016 | Niemeyer | |
| 9,568,584 B2 | 2/2017 | Shin | |
| 9,996,986 B2 | 6/2018 | Tan | |
| 10,003,928 B2 | 6/2018 | Nagpal | |
| 10,026,239 B2 | 7/2018 | Kim | |
| 10,173,671 B2 | 1/2019 | Seurer | |
| 2013/0038470 A1* | 2/2013 | Niemeyer | G01N 33/0075 340/870.11 |

(Continued)

FOREIGN PATENT DOCUMENTS

| | | | |
|---|---|---|---|
| DE | 20091013466 | 9/2010 | |
| WO | WO2014075080 | 5/2014 | |
| WO | WO-2017189361 A1 * | 11/2017 | ............ B60W 50/14 |

OTHER PUBLICATIONS

Miluzzo et al., "CaliBree: A Self-calibration System for Mobile Sensor Networks", International Conference on Distributed Computing in Sensor Systems DCOSS 2008: Distributed Computing in Sensor Systems pp. 314-331; Springer-Verlag Berlin Heidelberg 2008 (Year: 2008).*

(Continued)

*Primary Examiner* — Regis J Betsch
(74) *Attorney, Agent, or Firm* — Thomas W. Galvani, P.C.; Thomas W. Galvani

(57) ABSTRACT

A remote sensor calibration system remotely calibrates sensors of various types in an automated fashion. The remote sensor calibration system receives sensor output, associated with one or more locations and one or more times, from a sensor and its peer sensor population. The sensor output from the sensor and its peer sensor population is compared to generate a correction factor. The correction factor is transmitted to the sensor and used to calibrate the sensor. Communication will typically occur via one or more wireless links allowing the sensors to be remotely calibrate while maintaining their mobility.

17 Claims, 5 Drawing Sheets

(56) References Cited

U.S. PATENT DOCUMENTS

2019/0121782 A1    4/2019  Sun
2019/0277671 A1*   9/2019  Weissenmayer ..... G01D 18/002

OTHER PUBLICATIONS

Yun Xiang, "Mobile Sensor Network Design and Optimization for Air Quality Monitoring", Thesis Univ of Michigan 2014 (Year: 2014).*

* cited by examiner

REMOTE SENSOR CALIBRATION SYSTEM

CROSS-REFERENCE TO RELATED APPLICATION

This application claims priority to U.S. Provisional Patent Application No. 62/743,459, filed Oct. 9, 2018.

BACKGROUND OF THE INVENTION

1. Field of the Invention

The invention relates to sensor calibration and, in particular, to systems for calibration of sensors based on data collected from a population of similar or identical sensors operating in the same or similar area and timeframe and methods therefor.

2. Related Art

Air quality sensors (AQSs) are used in cars to control the car's recirculation flap position to prevent high levels of pollution from entering the car's cabin. For instance, an AQS system may issue recommendations for closing a recirculation flap to the central processing unit (CPU) of an air conditioning unit when pollution increases are detected. AQS systems can also issue recommendations for re-opening a recirculation flap when the outside air is cleaner. This method has been proven to reduce the average pollution in car cabins and is used in millions of cars each year.

One of the key characteristics of AQSs is their sensitivity to particular gases. Traditionally, AQSs typically detect volatile organic compound (VOCs) and nitrogen dioxide (NO2). However, like most sensors, AQS measurement characteristics are spread over a certain range. These characteristics also evolve over time.

The following references disclose sensor calibration techniques aimed at addressing these issues.

U.S. Pat. No. 9,332,322 discloses a climate sensor network whereby one sensor is used to calibrate other sensors.

U.S. Pat. No. 9,996,986 discloses sensor offset calibration using map information.

U.S. Patent Publication No. 2019/0121782 discloses a cognitive learning method whereby a calibration sensor is used to calibrate an itinerate sensor.

U.S. Pat. No. 4,155,038 discloses an automated comparison calibration device with ratio determination.

U.S. Pat. No. 10,003,928 discloses crowd-sourced passive positioning and calibration.

U.S. Pat. No. 9,568,584 discloses a wireless positioning server using clock offset calibration and a positioning method using the same.

U.S. Pat. No. 8,296,225 discloses time-efficient and deterministic adaptive score calibration techniques for maintaining a predefined score distribution.

German Patent Publication No. DE200091013466 discloses a method for automatic calibration of a navigation instrument utilized in a ship by automatically comparing measured data with measured data from a satellite navigation system as a reference.

PCT Patent Publication No. WO2014075080 discloses a crowd-sourced hardware calibration method.

From the discussion that follows, it will become apparent that the present invention addresses the deficiencies associated with the prior art while providing numerous additional advantages and benefits not contemplated or possible with prior art constructions.

SUMMARY OF THE INVENTION

Ideally, to optimize the function they fulfill, sensors would all have exactly the same performance metrics that would be perfectly stable overtime and perfectly reliable. However, this is not the case in reality. A remote sensor calibration system is disclosed herein to address these limitations.

A remote sensor calibration system operates automatically based on the comparison of one or more sensors to a peer sensor population. In this manner, the distribution of performance metrics such as a sensor sensitivity can be narrowed and thus improved. In addition, outlier sensors or defective sensors providing sensor output that is beyond calibration can be identified for repair or replacement. Using connected car features, or wireless personal devices, the remote calibration can occur continuously for various types of sensors.

Use of a remote sensor calibration system improves sensor performance spread. In addition, sensor performance is improved and sensor useful life is, on average, prolonged. Human intervention or vehicle service or recall is also reduced or eliminated, and the quality of data collected by sensors is improved. In the case of automotive AQSs, in use for mapping purposes, the quality of maps is improved by ensuring the data received by each sensor, is better calibrated. Maps can therefore be better correlated with absolute concentrations of contaminants, pollutants, or other physical properties.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
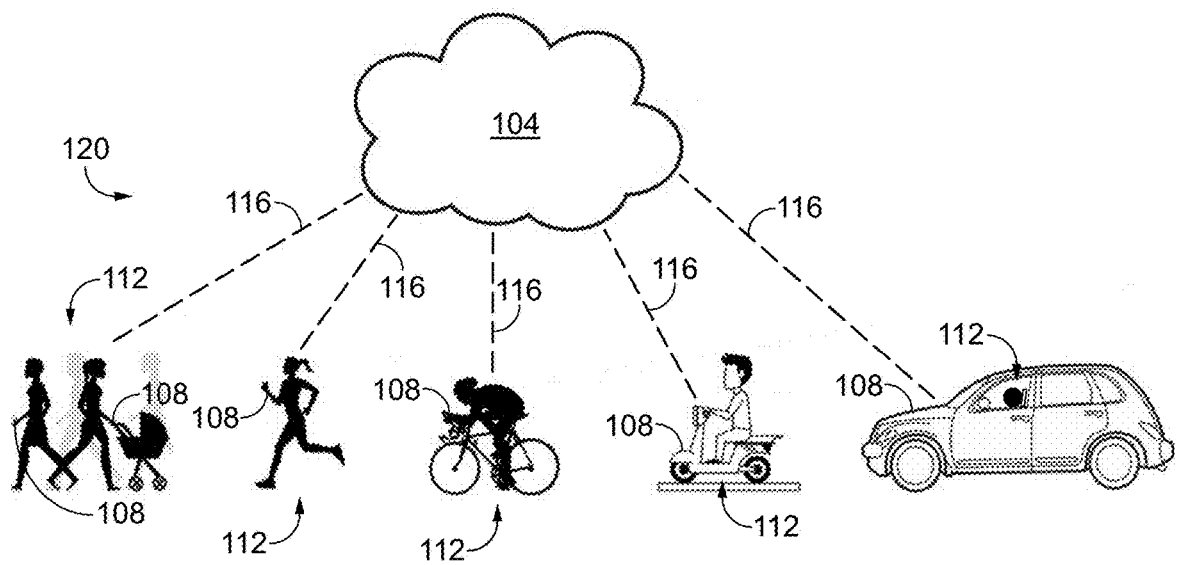
FIG. 1 is a block diagram illustrating an exemplary remote sensor calibration system in an environment of use.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The remote sensor calibration system herein remotely calibrates mobile sensors, such as vehicle sensors, wearable sensors or other sensors moving on or through roadways or city or rural environments. In one or more embodiments, the remote sensor calibration system will perform sensor calibration by comparing a sensor's output to the combined sensor output of a peer sensor population.

Peer sensors in a peer sensor population will typically be sensors measuring the same or similar physical property, operating in the same or similar areas and within a relevant period of time. The peer sensor population will typically be a large population of sensors providing sensor output that is sufficient to obtain statistically significant averages for a plurality of locations and timeframes. For example, in some circumstances 10 sensors at the same or similar location will be sufficient while, in other circumstances, 50 or more sensors will be preferable.

Typically, the sensors and the peer sensors in their peer sensor population referred to herein will share the trait that the sensor output thereof are expected to be statistically very similar, or identical to, when operating in the same or a similar environment in the same or similar time frame. For example, a sensor and its peer sensors may be sensors manufactured to identical specifications. As such, a sensor that is moving through the same or nearby locations at similar times, or at least relevant times, is expected to provide statistically similar or identical sensor output as its peer sensors.

Remote calibration using a peer sensor population, as disclosed herein, is advantageous for a number of reasons. For instance, it would be advantageous to vehicles equipped with an AQS, to rely on a sensor that is calibrated, better calibrated, regularly calibrated overtime, or various subsets thereof, without incurring the cost of a service or replacement.

In addition, vehicles use a variety of sensors that measure driving conditions, such as, temperature, relative humidity, sun load, rain, light, noise, etc. The spread or differences in their performance metrics from one sensor to the other, even immediately out of production, decreases the accuracy and reliability of their measurements and therefore degrades their function and the benefits to the users. For these reasons, most, if not all, sensors would benefit from a more accurate calibration that reduces the spread of their performance metrics, and a regularly occurring calibration that counteracts the effects of aging.

Data from a multitude of AQSs may be used for various reasons, such as to create pollution maps that are transmitted to vehicles in traffic, including those that do not have an onboard AQS, to optimize cabin air quality. The pollution map information that is subsequently transmitted back to vehicles, may be used to close a recirculation flap ahead of polluted areas, and open the recirculating flap when the pollution map information indicates that the vehicle is about to drive through a less polluted area.

The data from AQSs collected for mapping purposes includes information regarding pollution variations detected in traffic, with location information and time information. Pollution maps may be generated using information from multiple AQSs being driven through the same locations and times, so as to be statistically representative. Some AQSs will have lower sensitivities while others will have higher sensitivities. Since the maps are generated based on a multitude of sensors, the resulting pollution indicators generated for each location and time, are representative of the AQS population's average sensitivity.

To improve the accuracy of pollution maps, it would be beneficial to reduce the sensor population sensitivity spread. Indeed, sensors with much higher sensitivity than average, or much lower sensitivity than average, influence the pollution map information in one direction or the other, thereby introducing errors in the same.

Another advantage to remote calibration, as disclosed herein, is that it does not require any human intervention, which is typically costly. In addition, remote sensor calibration improves the performance of sensors, such as by improving sensor accuracy, precision, sensitivity, resolution, or various other performance metrics. Remote calibration via a remote sensor calibration system also does away with the need for laboratory equipment, service fees, or immobilization of a sensor for calibration purposes.

A remote sensor calibration system may calibrate AQSs, as well as other vehicle sensors, such as sun load sensors, humidity sensors, temperature sensors, rain sensors, wind sensors, noise/decibel, and other sensors. The remote sensor calibration system may also be used to calibrate non-vehicular and other sensors. For example, wearable or other sensors may be calibrated by a remote sensor calibration system. As can be seen, the sensors will typically be various types of portable or otherwise mobile sensors.

Calibration by a remote sensor calibration system results in improved sensor performance, which may be advantageously used for various purposes. For instance, in the case of automotive AQSs, remote calibration improves cabin air quality optimization for vehicles equipped with an onboard AQS. Calibration prevents an otherwise low sensitivity sensor from missing pollution peaks on a road or other area that would warrant recirculation flap closure prior to calibration. Conversely, calibration will keep an otherwise overly sensitive sensor from recommending excessive recirculation flap closures for pollution peaks that are actually not high enough to warrant recirculation flap closure. Calibration will also improve the quality of the pollution maps generated with data from a large population of AQSs.

As will be described further below, the calibration performed by a remote sensor calibration system will typically not be based on the sensor output of a single sensor relative to a single event, but on sensor output of a plurality of sensors for a plurality of events. For example, sensor output representing one or more measurements by a plurality of sensors may be compared to sensor output representing one or more measurements by the sensor to be calibrated. Typically, this comparison will be a statistical process rather than a simple comparison.

Referring to FIG. 1, in one or more embodiments, a remote sensor calibration system 120 may comprise one or more end point devices 108 and one or more servers 104 in communication with one another. As can be seen in FIG. 1, communication may occur via one or more communication links 116 between moving or stationary end point devices 108 and one or more servers 104 or central computers. It will be understood that a communication link 116, may comprise one or more wireless communication links, including cellular or other RF communication links. A communication link 116 may be wired as well, such as via an electrical or optical cable.

In operation, sensor data from various end point devices 108 may be transmitted to a remote server 104 via one or more communication links 116. As will be described further below, sensor data may comprise or consist of sensor output from one or more sensors at or accessible to the end point devices 108.

As can be seen from FIG. 1, an end point device 108 may be a car, bike, or other vehicle, with one or more onboard sensors, which may be driven by users 112. In addition, an end point device 108 may be a portable or mobile device, such as a smartphones, laptop, wearable, or other mobile computing device. It is contemplated that an end point device 108 may also be a sensing device comprising one or more sensors and communication devices. As alluded to in the foregoing, end point devices 108 will typically be mobile. For example, an end point device 108 may move inside or outside a city or other defined area or boundary, such as by being carried by a user or vehicle.

Figure 2:
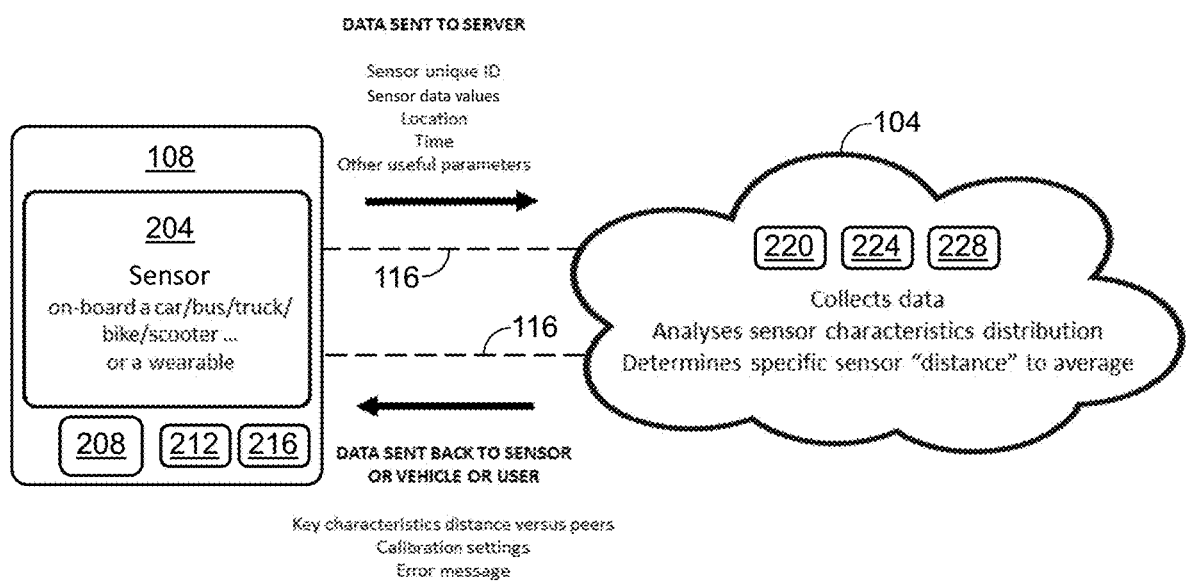
FIG. 2 is a block diagram illustrating an exemplary end point device and server in an environment of use.

FIG. 2 illustrates an exemplary end point device 108 and server 104, and communication therebetween. In one or more embodiments, sensor data may be transmitted from an end point device 108 to a server 104, while calibration data may be transmitted from a server to an end point device.

As can be seen, in addition to sensor output from a sensor 204, sensor data may include a unique identifier for an end point device 108, its one or more sensors, or both. Sensor data may also include location information identifying for a sensor 204 or end point device 108, time, and other information.

Sensor output may comprise or consist of one or more data values that represent one or more measurements of some quantity or characteristic by a sensor. This will typically be a physical property. To illustrate, an AQS may output a pollution peak, a noise sensor or microphone may output a decibel level, a temperature sensor may output a temperature measurement, a light sensor may output a luminance measurement, etc. Data values may be represented in sensor output by digital or analog signals.

Calibration data may include one or more correction factors, such as distances or offsets, used to adjust a sensor's sensor output, thereby calibrating the sensor. For example, a server 104 may analyze the distribution of sensor output from a peer sensor population and determine a correction factor, relative to the peer sensor population average, for a sensor undergoing calibration.

Assuming that the average of the sensor output of a population of peer sensors is more precise and reliable than the output of a single sensor, the distance between the sensor output of the single sensor and the peer sensors can be used as a correction factor to improve performance of the sensor. The correction factor may be generated at a server 104 and provided to end point devices 108 by the server. Calibration of a sensor 204 can then occur at the end point devices 108.

Calibration data may also include various other data. For instance, the distance from a sensor 204 to one or more of its peer sensors in space, time, or both may be included. In addition, error codes or messages may be provided by a server 104 within the calibration data.

In FIG. 2, the server 104 is illustrated as a cloud to indicate that a "server" may be a collection of one or more individual servers, appliances, computing devices, associated network infrastructure, or various subsets thereof. Individual servers 104 may be computers or other computing devices in one or more embodiments. A server 104, such as via a processor 220 thereof, may execute machine readable code integrated in its processor or stored on a non-transient storage device 224 (excluding carrier waves or other signaling) to provide the functionality disclosed herein.

One or more storage devices 224 may be part of a server 104, be remotely accessible to a server, or both. Some exemplary storage devices 224 include, solid state drives, hard drives, optical storage, flash memory, and the like. Some exemplary processors 220 include, microprocessors, microcontrollers, FPGA, ASICS, integrated circuits, and the like.

FIG. 2 also illustrates components of an exemplary end point device 108. In one or more embodiments, an end point device 108 may comprise one or more processors 208. A processor 208 may execute machine readable code to provide the functionality disclosed herein. This machine readable code may be integrated into a processor 208 or stored on a non-transient storage device 212 (excluding carrier waves or other signaling) for retrieval and execution by a processor 208.

Some exemplary processors 208 include, microprocessors, microcontrollers, FPGA, ASICS, integrated circuits, and the like. A storage device 212 may be part of an end point device 108, be remotely accessible to an end point device, or both. Some exemplary storage devices 212 include, solid state drives, hard drives, optical storage, flash memory, and the like.

One or more communication devices 216, 228 will be included to transmit data, receive data, or both via one or more communication links 116. For example, communication devices 216, 228 may communicate sensor data, calibration data, or other data via one or more communication links 116. Some exemplary communication devices include wired and wireless network interfaces, such as cellular, cable, or other modems, RF transceivers, optical transceivers, and the like.

As described above, an end point device 108 will comprise or be in communication with one or more sensors 204, such as the AQS and other types of sensors described above. Sensors may be considered peer sensors regardless of the type of end point device they are associated with. It is contemplated that the remote sensor calibration system herein may collect sensor output from any group of end point devices 108 or sensors 204, now known or later developed, to calibrate one or more sensors. Though calibration will typically only occur between sensors manufactured to identical specifications (i.e., peer sensors), it is contemplated that this need not be the case in every circumstance.

Figure 3:
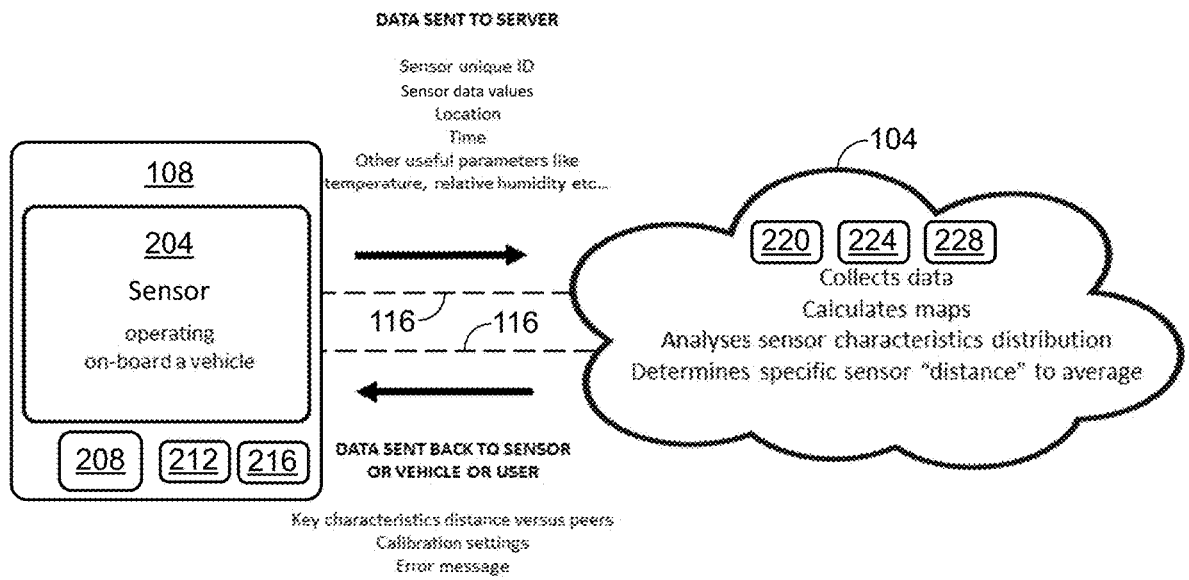
FIG. 3 is a block diagram illustrating an exemplary end point device and server in an environment of use.

FIG. 3 illustrates another exemplary end point device 108 and server 104. Namely, FIG. 3 illustrates communication of data between an automotive or vehicular end point device 108 and a server 104 via one or more communication links 116. In this example, the sensor 204 is an AQS. It is contemplated that sensor output from such sensor 204 may include data values for temperature, relative humidity, particulate, and other measurements in addition to pollution peaks. These environmental properties may be measured by other types of sensors 204 as well in both automotive and non-automotive applications.

Figure 4:
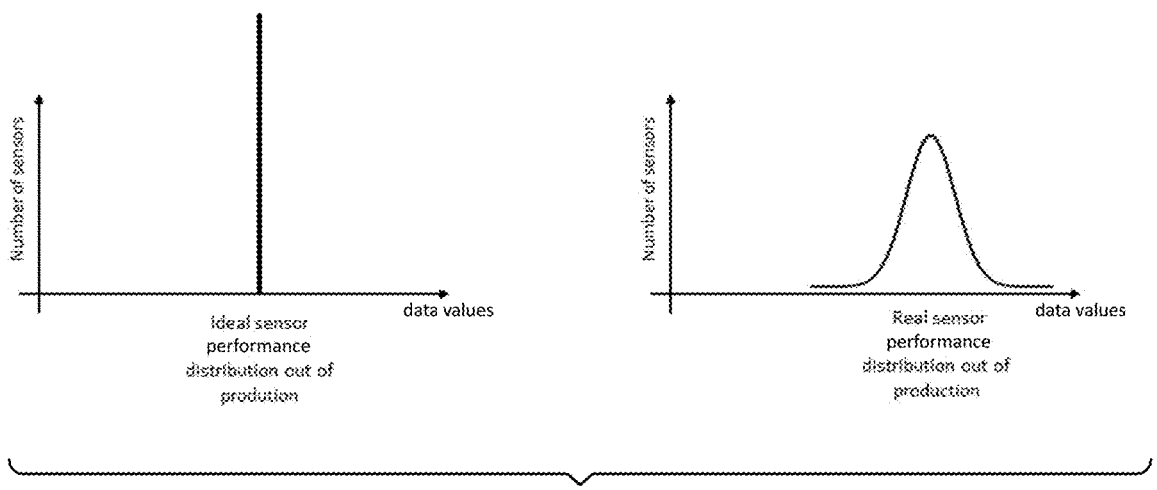
FIG. 4 illustrates an ideal distribution and a real distribution of exemplary sensor output.

FIG. 4 illustrates the difference between an ideal data value distribution, where all sensors perform identically, and a real distribution, where some variation in sensor output is present. As can be seen by the ideal distribution in leftmost graph, all sensors manufactured to identical specifications ideally provide sensor output having the same data values for the same environmental characteristic or other property being "sensed" or otherwise measured. In practice however, measurements provided by sensors, even those manufactured to identical specifications, vary, as shown by the real distribution in the rightmost graph. The two distributions of FIG. 4 also show that sensor output precision and reliability can be increased or maximized using the average of a real distribution.

Figure 5:
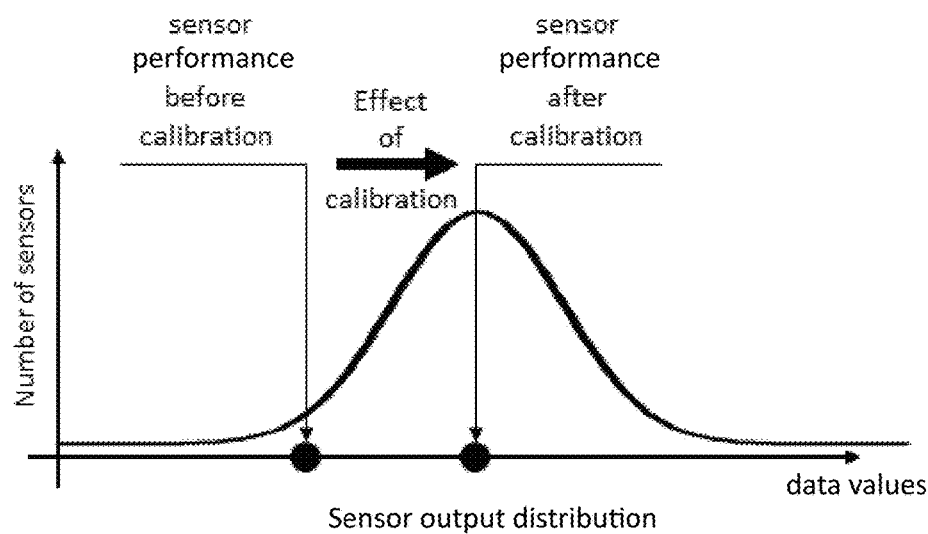
FIG. 5 illustrates effectiveness of an exemplary sensor calibration by a remote sensor calibration system.

FIG. 5 illustrates an advantage of a remote sensor calibration system. As can be seen, calibration data, such as a distance, offset, or other correction factor, may be used to calibrate sensors producing data values below or otherwise outside of average, such that these sensors' sensor output are close or very close to their peer sensor population average. For example, calibration data may include a numerical correction factor that is applied to bring a sensor's data value closer to its peer sensor population's average.

It is noted that outlier sensors that are either too sensitive or not sensitive enough, beyond a predefined threshold may be identified via a remote sensor calibration system. For example, an overly sensitive sensor may produce data values that are too high for a given quantity, while an abnormally insensitive sensor may produce data values that are too low for a given quantity. A server may identify sensors reporting data values outside a predefined threshold as outliers. For example, sensors reporting data values that are, on average, outside a predefined threshold or range may be identified as outliers. This predefined threshold may be based on a correction factor in one or more embodiments. For example, a predefined threshold may be a predetermined difference or distance from the peer sensor population average. A predefined threshold may provide a range for identifying outliers in some embodiments, such as by providing a predetermined upper and lower bound relative to the peer sensor population average.

While some of these sensors can be identified for calibration purposes, it is also possible to identify such outlier sensors for other reasons. For example, a user may be sent a maintenance or other notification, so that the user can decide to repair or replace an outlier sensor. In the case of an AQS or other vehicular sensor, a diagnostics message may be recorded by the vehicle such that the same may be read at the OBDII port, so the outlier sensor may be repaired or replaced at the next service. An outlier sensor's output may also be ignored or discarded within its peer sensor population for purposes of determining peer sensor population averages, pollution map generation, or other purposes.

Outlier sensor output may also be ignored or discarded. In general, outlier sensor output may be sensor output outside of a predefined threshold (which as described above may be a range providing an upper and lower bound). As noted above, the predefined threshold may be a predetermined difference or distance from the peer sensor population average. A sensor need not be an outlier sensor for its sensor output to be an outlier.

Figure 6:
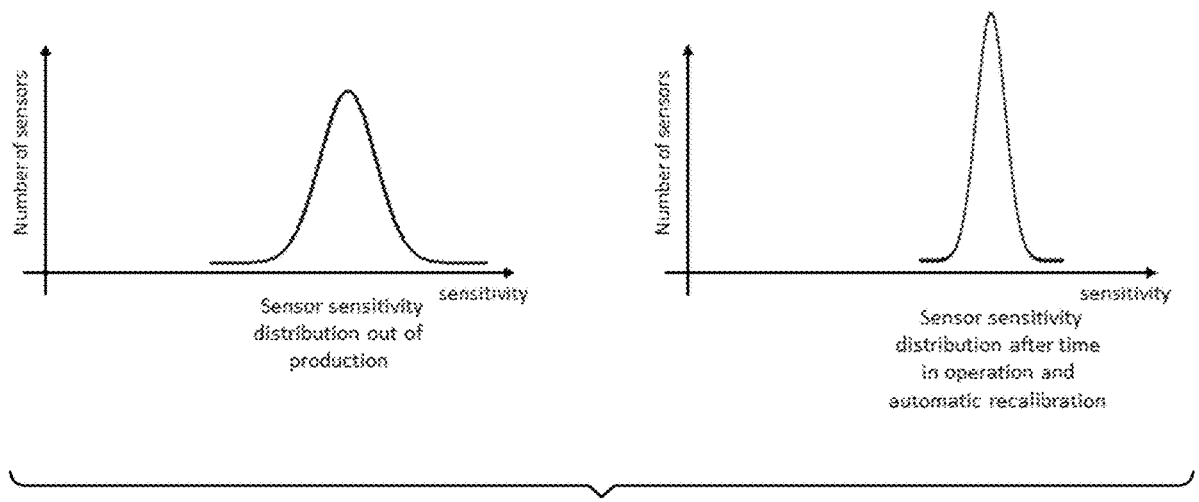
FIG. 6 illustrates effectiveness of an exemplary sensor population calibration by a remote sensor calibration system.

FIG. 6 illustrates another advantage of a remote sensor calibration system. As can be seen, calibration of a plurality of sensors in a sensor population results in a performance distribution spread that is substantially narrowed. This improves the quality of the sensor output. Though shown in FIG. 6 as improving sensor sensitivity, sensor accuracy, precision, reliability, or other performance metrics may be improved via calibration by a remote sensor calibration system.

Figure 7:
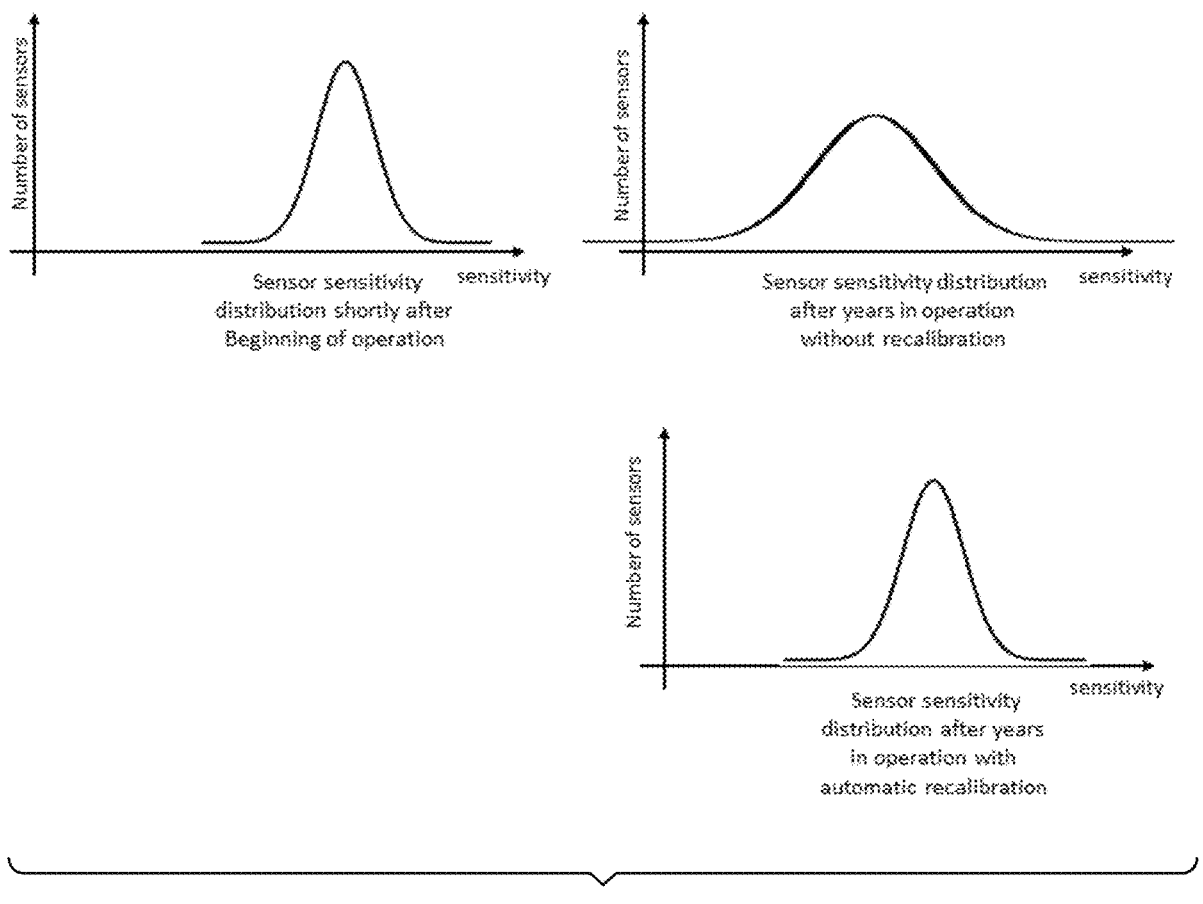
FIG. 7 illustrates effectiveness of an exemplary sensor calibration by a remote sensor calibration system.

FIG. 7 illustrates yet another advantage of calibration of a plurality of sensors. In FIG. 7, the performance distribution of a plurality of sensors has broadened over time. Calibration improves the performance distribution by totally or partially countering the effect of sensor aging. Though illustrated as improving sensitivity in FIG. 7, sensor accuracy, precision, reliability, or other performance metrics may be improved via calibration by a remote sensor calibration system.

Figure 8:
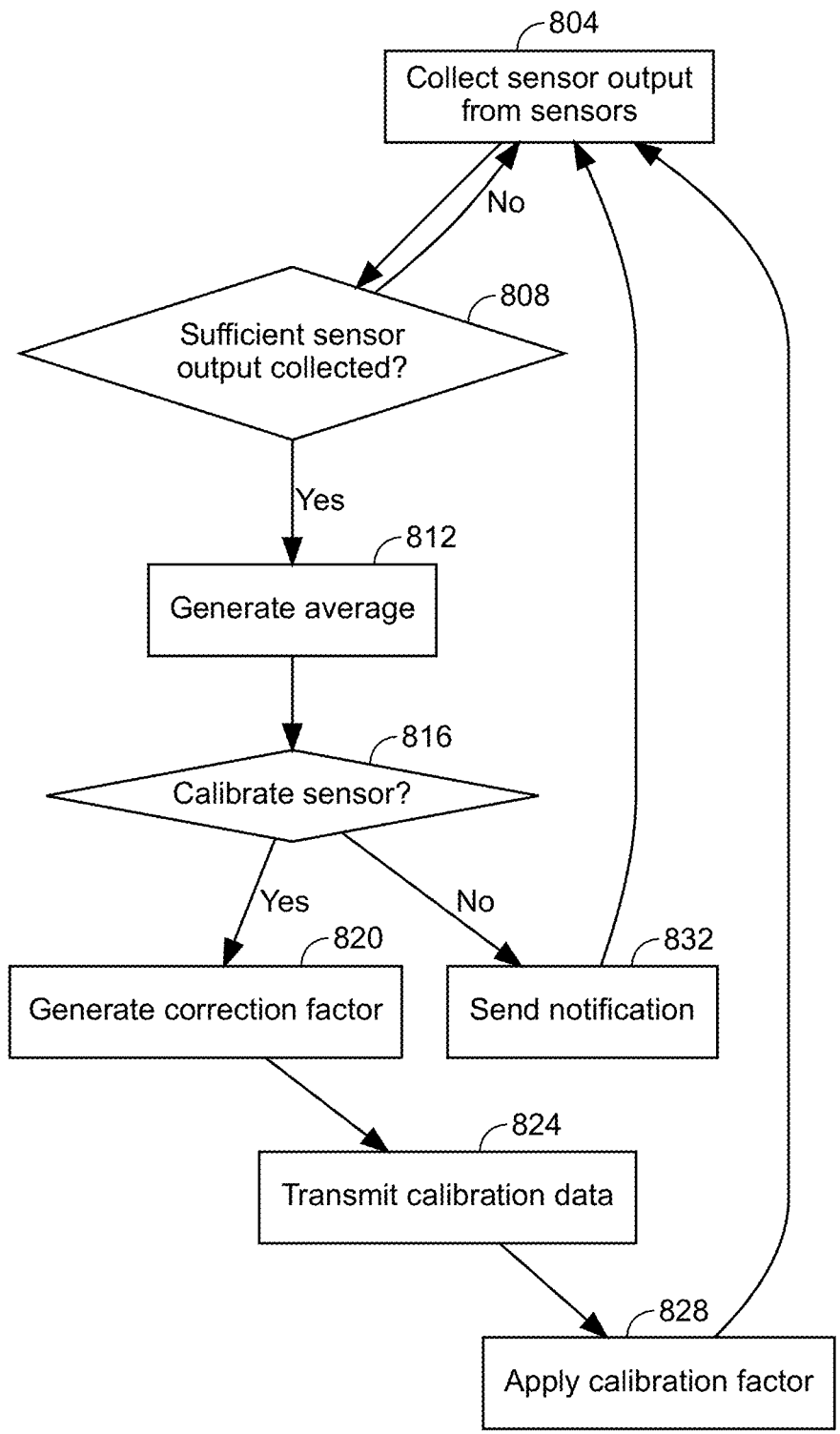
FIG. 8 is a flow diagram illustrating operation of an exemplary remote sensor calibration system.

Operation of an exemplary remote sensor calibration system will now be described with regard to FIGS. 1-3 and 8. FIG. 8 illustrates operation of an exemplary remote sensor calibration system. The steps of FIG. 8 may be performed by a server 104 in one or more embodiments. Though shown in a particular sequence it is contemplated that steps of the invention may occur in different sequences in the various embodiments of the invention.

In one or more embodiments, a remote sensor calibration system 120 comprises a plurality of sensors 204 at one or more end point devices 108. Such end point devices 108 may be vehicles, carried by persons, or otherwise be mobile, and measure one or more physical properties while moving within a common area continuously, or over overlapping periods of time or periods of time that are otherwise similar or relevant to each other, such as the statistically equivalent times discussed below.

At a step 804, sensor output may be collected from a plurality of sensors 204. Typically, these sensors 204 will be peer sensors, namely, sensors that have been manufactured to identical specifications. When collecting sensor output, end point devices 108 may communicate sensor output, sensor data, or both with a server 104, for example via one or more communication links 116. As stated above, sensor data may include location information and time information, respectively indicating the location and time for which the sensor output was generated.

Collection of sensor output may take place over a period of time, with sensor output from individual sensors 204 being transmitted to and received by a server 104 to collect the sensor output. A server 104 may receive or be transmitted sensor output from one or more sensors 204, end point devices 108, or both on a periodic or other regular basis. It is noted that sensor data, sensor output, or both may be stored on one or more storage devices of a server 104 in one or more embodiments.

At a decision step 808, it may be determined whether sufficient sensor output has been collected. In general, sufficient sensor output has been collected when the received sensor output can be used to determine where the performance metrics of individual sensors 204 stand versus the overall peer sensor population. In one or more embodiments, sufficient sensor output has been collected when statistically significant averages of sensor output for at least one location and time or timeframe can be generated.

If the collected sensor output is not yet sufficient at decision step 808, additional sensor output may be collected at step 804. If the collected sensor output is sufficient, one or more calibration targets may be generated at a step 812. In one or more embodiments, a calibration target may be an average of the collected sensor output. Sensor output from outlier sensors may be ignored in generating a calibration target. In addition, outlier sensor output may also be ignored in generating a calibration target.

In one or more embodiments, an average may be calculated with the sensor output from a population of peer sensors. This peer sensor population average is based on sensor output from multiple peer sensors and typically on multiple locations and times for each sensor. The average may be a simple average, or a weighted average whereby more weight is assigned to some sensors or sensor output over others, depending on various criteria. Some exemplary criteria include the age of the sensor, its distance, or history of distance from the peer population average, as well other characteristics of its sensor output.

Typically, sensor output representing a measurement of a particular property will be grouped together for averaging to generate a calibration target for the property. For instance, pollution peak data values may be grouped and averaged together to generate a calibration target for the same.

Grouping of sensor output may be based on relevancy or relatedness in the location, time, or both associated therewith as well. Locations must typically be close enough to be estimated or determined to be statistically equivalent in terms of sensor output. Times need not always be close in the sense that they are within predefined period of one another. Rather, times may be deemed statistically equivalent, and therefore relevant, if they are within a predefined period of time on similar days. For example, 7:59 am on a Tuesday of a regular workday, and 7:58 am the next Tuesday may be considered statistically equivalent in one or more embodiments.

Some care must be taken when determining what times are statistically equivalent since the sensor output can be influenced by external factors like the wind, rain, or other weather or external effects. Again, sensor output may also be ignored or discarded by an end point device 108 or server 104 when such external effects are present, when the sensor output or a sensor itself is an outlier, or both.

The notion of statistical equivalence with regard to time will typically also depend on the type of sensors 204. For instance, an AQS will tend to have a similar output on average for the same location on a daily pattern. In other words, a Tuesday morning at 8:00 am will tend to generate sensor output measuring pollution similar to other Tuesday mornings at 8:00 am, once the effect of unpredictable external factors is removed.

The same is not true for temperature because temperature can be very different from one Tuesday to another. The selection of statistically equivalent times must therefore be made based on the type of sensor.

At a decision step 816, it may be determined whether sensor calibration should occur for one or more sensors 204. This may occur in various ways. In one or more embodiments, sensors 204 may be calibrated without human intervention. This may occur, for example, by automatically calibrating one or more sensors 204 after sufficient sensor output has been collected, as described above. In addition, calibration may be performed automatically on a periodic or other regular basis to ensure the sensors 204. For example, a sensor 204 in an end point device 108 comprising a vehicle may be calibrated every month or every 1000 miles, such as to counter the effects of aging.

Calibration may occur automatically for all sensors 204 or a subset thereof. For example, in addition to the above, calibration may occur for sensors 204 providing sensor output that is outside a predefined threshold from the peer sensor population average. This may be determined by a server 104 in one or more embodiments.

At a step 820, a correction factor may be generated for use in calibrating one or more sensors 204. In one or more embodiments, sensor output, over a period of time, may be compared to the average sensor output from peer sensors in a peer sensor population operating in the same or relevant locations and times. Accordingly, this comparison typically does not occur between one sensor and another sensor, but rather, between one sensor and a peer sensor population that is sufficiently large to be statistically significant. The comparison will typically also be based on sensor output at multiple locations, times, or both, as opposed to sensor output for a single event, location, or time.

The difference or offset between a particular sensor's output and its peer sensor population's average sensor output may be used as a correction factor in one or more embodiments. This is illustrated in FIG. 5. A correction factor may be a positive or negative numerical value that is multiplied or added to sensor output to bring the sensor output closer to a peer population average.

The correction factor may be transmitted as or within calibration data at a step 824. As described above, such transmission may be made by a server 104 to an end point device 108 having or associated with the sensor 204 that is to be calibrated.

At a step 828, a correction factor may be applied to calibrate a sensor 204. In one or more embodiments, calibration may involve changes or updates to software, hardware, or both. For example, a software calibration may modify sensor output by adding, multiplying or otherwise applying a correction factor, while a hardware calibration may occur by modifying the gain of sensor output. A software calibration may occur at an end point device 108, at a sensor 204 itself, or at a server 104. A hardware calibration will typically occur at an end point device 108 or at a sensor 204 itself.

Referring back to decision step 816, sensor calibration may not always occur. For example, it may be determined that a sensor is an outlier or otherwise cannot or should not be calibrated. In such case, other steps may be taken. As shown in FIG. 8, a notification is transmitted at step 832 to an end point device. The notification may include diagnostic information indicating, among other things, that the sensor is an outlier or is otherwise defective. This will allow remedial measures to be taken, such as described above.

As described above, a sensor 204 may be a temperature sensor, or humidity sensors, or rain sensors, or sun load sensors. These sensors 204 may be installed in a vehicle during manufacturing and are expected to function for the whole life of the vehicle. Calibration of such sensors 204 may occur by changing their bias, sensitivity, or another parameter that is affecting their sensor output. This can occur purely via a software update, but it may also occur by altering some of the sensor hardware operation via a software or firmware update. For example, a sensor output may be shifted by a calculated correction factor, or a sensor output gain may be multiplied or divided by a calculated correction factor.

Also as described above, a sensor 204 may also be an AQS used to minimize the pollution entering a vehicle's cabin by controlling the position of the recirculation flap. Such sensors 204 typically detect variations of pollution with time. Their sensitivity is therefore a key performance metric. Sensitivity can be spread, out of production, over a range with a width of, for example, a factor of two.

AQSs are typically not calibrated, to keep their cost low. It is therefore advantageous to calibrate these sensors remotely and automatically as described herein. As a result, the sensitivity distribution over a population of AQSs is narrower and accordingly improved.

As an example, an AQS detects, on average, over 60 days, on a specific 1-mile portion of highway, between 7:30 am and 8:00 am on weekdays, pollution peaks with an average amplitude of 40%. Over the same periods of time and area, a population of 100 other AQSs detect, on average, pollution peaks with an amplitude of 80%. After calculating these two averages, the server will compare them and will conclude that the AQS being tested has a sensitivity on average 50% lower than its peers.

Once the server has identified where one or more sensor performance metrics stand in relation to the peer sensor population distribution, it can generate calibration data including a correction factor that can then be transmitted back to each end point device, so the sensor thereof can be calibrated with the same.

In the above example, the server would output a correction factor, for the sensitivity of the sensor being tested, that corrects its sensitivity by a factor of two. After the correction, the sensor would therefore behave on average, like an average sensor in its peer sensor population.

As described above, calibration may occur by adjusting the sensor firmware or software, or by adjusting its hardware operation in a corresponding manner. It is noted that a sensor itself, or its end point device, can perform this calibration based on the calibration data received from a server. The calibration adjusts sensor output such that it is closer to its peer sensor population's average, and therefore narrows the entire sensor population's distribution. This leads to more accurate or efficient sensor function, and a more homogenous function at the end point devices. The distribution in key sensor performance metrics is accordingly also reduced.

In the exemplary case described above, the key performance metric to be calibrated is sensitivity. It is noted that the remote sensor calibration system can also calibrate other sensor performance metrics like offset, linearity, response time, etc.

In one embodiment, the sensor output of AQSs calibrated by a remote sensor calibration system are used to create high-resolution traffic pollution maps. In this case, the remote automatic calibration method presents an advantage in that it improves the quality of the sensor output and therefore the accuracy of the resulting maps is also improved.

Pollution maps may be generated for each of a plurality of locations and times. For example, 96 maps per day, in 15-minute increments, each on a grid of approximately seventy thousand locations for a city of approximately five hundred square kilometers. Such maps could be calculated, for weekdays, weekends, or other time periods. Remote calibration of sensors by a remote sensor calibration system herein can also therefore be described as comparing an individual sensor's contribution to a particular resulting pollution level for one location on one of the 96 maps, to this pollution level on the map, that was obtained by taking into account contributions from a multitude of sensors and events.

Sensors or sensor output that are found to be too far away from the peer sensor population average can be discarded for mapping purposes. This further improves the quality of pollution maps. In addition, sensors that are deemed to be non-functional can receive a flag from the server, that can be stored in the car diagnostics log, such as to allow the sensor to be repaired or replaced at the next service. If a sensor is key to vehicle safety or main function, a warning can also be presented, such as on the vehicle's dashboard.

In another embodiment, a server may be provided at one or more end point devices. In such case, sensor output may be instead directly transmitted from vehicle to vehicle (V2V) so the comparison to a peer sensor population comparison may occur at the vehicle or other end point. A vehicle can store comparison data, such as sensor output and sensor data, for a certain period of time, until enough data is available to determine whether sensor calibration should occur.

For example, if a vehicle exchanged external temperature information with other adjacent end point devices in traffic for 3 months, and found that more than 95% of the time its temperature value is 2 degrees higher than such peer sensor population, it could advantageously decide to automatically calibrate its sensor to be more in line with the peer sensor population average. This calibration process may be used with other sensors and performance metrics as well, such as AQSs and their sensitivity.

In another embodiment, the comparisons between the sensor output of the sensor being tested and other sensors, do not have to occur for close or identical times (synchronous), but instead, they can occur for statistically equivalent times. For example, the data of a first AQS, on a Monday at 8:32 am, at a location, can be compared to the data from a population of other AQSs, on other similar Mondays (provided that they are not holidays for example) at 8:32 am+/−5 minutes, at this location. Broadening the relevancy or relatedness of sensor output to include similar timeframes, rather than limiting them to identical times, increases the number of comparison points, and therefore improves the statistical significance of the comparisons and the quality of the calibrations.

Indeed, substantially all sensor output should be similar, for a specific time of day, type of day (weekend, holiday, weekdays, . . . ), and location if pollution patterns are more or less repeatable for similar days and similar times. The sensor output may be adjusted for varying external effects such as air temperature, wind, etc. Temperature can be very different from one day to the other, and such differences may affect sensor output. A simple temperature compensation may be applied to sensor output in such cases.

Similarly, the locations used for comparison need not be strictly identical but can instead be within a distance that is small enough to be estimated or known not to have any significant effect on the characteristic or other physical property being measured. For example, the temperature or humidity measured on a roadway, may not be expected to vary significantly within an average distance of 100 meters. In the case of the detection of pollution, a similar reasonable distance can be established, within which a plurality of AQSs should, on average, detect similar variations.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A remote sensor calibration system comprising:
a plurality of mobile sensors lacking reliable calibration, wherein the plurality of mobile sensors generate sensor output representing a plurality of measurements of at least one physical property associated with one or more locations and one or more times; and
one or more servers in communication with the plurality of mobile sensors, wherein the one or more servers:
continuously receive the sensor output from a first sensor, the first sensor being one of the plurality of mobile sensors and at an end point device;
continuously receive the sensor output from a plurality of second sensors, the plurality of second sensors being a subset of the plurality of mobile sensors and distinct from the first sensor;

select the sensor output from the first sensor and from the plurality of second sensors that only includes the sensor output associated with statistically-equivalent locations and times, herein defined as a selected first sensor output set and a selected second sensor output set, respectively;

when the selected first and second sensor output sets are sufficiently large, generate a correction factor based on a comparison of an average of the selected first sensor output set and an average of the selected second sensor output set, in response to a difference between the average of the selected first sensor output set measuring beyond a predefined threshold relative to the average of the selected second sensor output set, and transmit the correction factor to the end point device; wherein the first sensor is calibrated using the correction factor.

2. The remote sensor calibration system of claim 1, wherein the plurality of mobile sensors are manufactured to identical specifications.

3. The remote sensor calibration system of claim 1, wherein the plurality of mobile sensors are air quality sensors.

4. The remote sensor calibration system of claim 1, wherein the first sensor is calibrated by applying the correction factor to the sensor output of the first sensor.

5. The remote sensor calibration system of claim 1, wherein the correction factor is generated and transmitted to the end point device on a periodic basis to calibrate the first sensor.

6. The remote sensor calibration system of claim 1, wherein the sensor output from the first sensor indicates a sensitivity of the first sensor and calibration using the correction factor calibrates the sensitivity of the first sensor.

7. The remote sensor calibration system of claim 1, wherein the one or more servers transmit a notification to the end point device when the average of the selected first sensor output set is beyond the predefined threshold.

8. A remote sensor calibration system for calibrating a plurality of mobile sensors that generate sensor output representing a plurality of measurements of at least one physical property associated with one or more locations and one or more times, the remote sensor calibration system comprising:

one or more servers in communication with the plurality of mobile sensors, wherein the one or more servers:
continuously receive the sensor output from a first sensor, the first sensor being one of the plurality of mobile sensors and at an end point device;
continuously receive the sensor output from a plurality of second sensors, the plurality of second sensors being a subset of the plurality of mobile sensors and distinct from the first sensor;
select the sensor output from the first sensor and from the plurality of second sensors that only includes the sensor output associated with statistically-equivalent locations and times, herein defined as a selected first sensor output set and a selected second sensor output set, respectively;
when the selected first and second sensor output sets are sufficiently large, generate a correction factor based on a comparison of an average of the selected first sensor output set and an average of the selected second sensor output set, in response to a difference between the average of the selected first sensor output measuring beyond a predefined threshold relative to the average of the selected second sensor output; and
transmit the correction factor to the end point device; wherein the first sensor is calibrated using the correction factor.

9. The remote sensor calibration system of claim 8, wherein communication with the plurality of mobile sensors occurs via one or more wireless communication links.

10. The remote sensor calibration system of claim 8, wherein the first sensor is calibrated by applying the correction factor to the sensor output of the first sensor.

11. The remote sensor calibration system of claim 8, wherein the correction factor is generated and transmitted to the end point device on a periodic basis to calibrate the first sensor.

12. The remote sensor calibration system of claim 8, wherein the sensor output from the first sensor indicates a sensitivity of the first sensor and calibration using the correction factor calibrates the sensitivity of the first sensor.

13. The remote sensor calibration system of claim 8, wherein the one or more servers ignore the average of the selected first sensor output set when the average of the selected first sensor output set is beyond the predefined threshold.

14. The remote sensor calibration system of claim 8, wherein the one or more servers transmit a notification to the end point device when the average of the selected first sensor output set is beyond the predefined threshold.

15. The remote calibration system of claim 8, wherein the one or more servers are at a mobile end point device.

16. A remote sensor calibration system comprising:
a plurality of mobile sensors lacking reliable calibration, wherein the plurality of mobile sensors generate sensor output representing a plurality of measurements of at least one physical property associated with one or more locations and one or more times; and
one or more servers in communication with the plurality of mobile sensors, wherein the one or more servers:
continuously receive the sensor output from a first sensor, the first sensor being one of the plurality of mobile sensors;
continuously receive the sensor output from a plurality of second sensors, the plurality of second sensors being a subset of the plurality of mobile sensors and distinct from the first sensor;
select the sensor output from the first sensor and from the plurality of second sensors that only includes the sensor output associated with statistically-equivalent locations and times, herein defined as a selected first sensor output set and a selected second sensor output set, respectively;
when the selected first and second sensor output sets are sufficiently large, generate a correction factor based on a comparison of an average of the selected first sensor output set and an average of the selected second sensor output set in response to a difference between the average of the selected first sensor output set measuring beyond a predefined threshold relative to the average of the selected second sensor output; and
correct the sensor output of the first sensor using the correction factor to generate more accurate sensor output.

17. The remote sensor calibration system of claim 16, wherein the average of the selected first sensor output set is ignored when the average of the selected first sensor output set is beyond the predefined threshold.

* * * * *